United States Patent
Ho

(10) Patent No.: US 6,301,799 B1
(45) Date of Patent: Oct. 16, 2001

(54) ELECTRONIC FAT GAUGE

(76) Inventor: Charles Ho, 10F, No. 380, Sec. 1, Fu Shing South Road, Taipei (TW)

(*) Notice: Subject to any disclaimer, the term of this patent is extended or adjusted under 35 U.S.C. 154(b) by 0 days.

(21) Appl. No.: 09/521,482

(22) Filed: Mar. 9, 2000

(51) Int. Cl.⁷ ................................................. A61B 5/103
(52) U.S. Cl. ......................... 33/807; 33/512; 33/558.01; 600/587
(58) Field of Search ............................ 33/783, 784, 792, 33/793, 794, 797, 798, 800, 801, 807, 511, 512, 558.01, 558.2, 558.4, 1 N, 1 PT, 534; 600/587

(56) References Cited

U.S. PATENT DOCUMENTS

| | | | | |
|---|---|---|---|---|
| 1,644,967 | * | 10/1927 | Wettrich | ................................. 33/800 |
| 3,386,173 | * | 6/1968 | Kiralfy | ................................. 33/800 |
| 4,127,112 | * | 11/1978 | Sherlock et al. | ....................... 33/512 |
| 4,315,372 | * | 2/1982 | Kinkead | ................................. 33/798 |
| 5,430,954 | * | 7/1995 | Best et al. | ............................... 33/797 |

* cited by examiner

Primary Examiner—Andrew H. Hirshfeld
(74) Attorney, Agent, or Firm—Dougherty & Troxell

(57) ABSTRACT

An electronic fat gauge includes a main body and a clamping lever pivotally mounted on the main body. The clamping lever includes a shorter depressing arm and a longer measuring arm extended from a middle pivot portion of the clamping lever in opposite directions. When the shorter depressing arm is depressed, the longer measuring arm is caused to open by a wide angle relative to the main body for conveniently clamping a fatty area of a user's body between the measuring arm and the main body. The open angle of the measuring arm is converted into a signal through a variable resistor connected to the middle pivot portion of the clamping lever, and the signal is further converted by a control circuit into a value of measuring result for showing in a liquid crystal display and viewing by the user.

3 Claims, 6 Drawing Sheets

ELECTRONIC FAT GAUGE

BACKGROUND OF THE INVENTION

The present invention relates to an electronic fat gauge, and more particularly to an electronic fat gauge that uses a clamping lever to clamp a fatty area of a user's body and a variable resistor and a control circuit to convert an open angle of the clamping lever into a value of measurement that is shown in a liquid crystal display for easy viewing by the user.

The fat gauge is an aid for body slimming. There is a scissors-shaped mechanical fat gauge commercially available in the market. This type of fat gauge includes leading jaws for clamping a fatty area of a user's body and rear turning arms that are opened by an angle when the leading jaws open the same angle to clamp the fatty area. A cyclograph is provided at a vertical end portion of the rear turning arms and an index table is provided on the cyclograph. The user finds an index on the cyclograph corresponding to the openness of the rear turning arms and then compares the index with information about age and sex listed in an index contrast table additionally provided along with the fat gauge. A result from the comparison of the index with the age/sex information tells the user whether he or she needs body slimming to remove extra fat. For example, when a measured result indicates too much fat at the user's belly or upper arms, the user may take suitable actions to remove fat at these areas. This mechanical type fat gauge is inconvenient to handle and it is troublesome for the user to check the index contrast table for final information about the measurement.

SUMMARY OF THE INVENTION

It is therefore a primary object of the present invention to provide an electronic fat gauge that can be easily handled to measure any fatty area of a user's body and any measured result may be directly shown on the gauge for viewing by the user.

The electronic fat gauge according to the present invention for achieving the above and other objects mainly includes a main body and a clamping lever pivotally mounted on the main body. The clamping lever includes a shorter depressing arm and a longer measuring arm extended from a middle pivot portion of the clamping lever in opposite directions. When the shorter depressing arm is depressed, the longer measuring arm is caused to open by a wide angle relative to the main body for conveniently clamping a fatty area of a user's body between the measuring arm and the main body. The open angle of the measuring arm is converted into a signal through a variable resistor connected to the middle pivot portion of the clamping lever, and the signal is further converted by a control circuit into a value of measurement for showing in a liquid crystal display on the main body.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
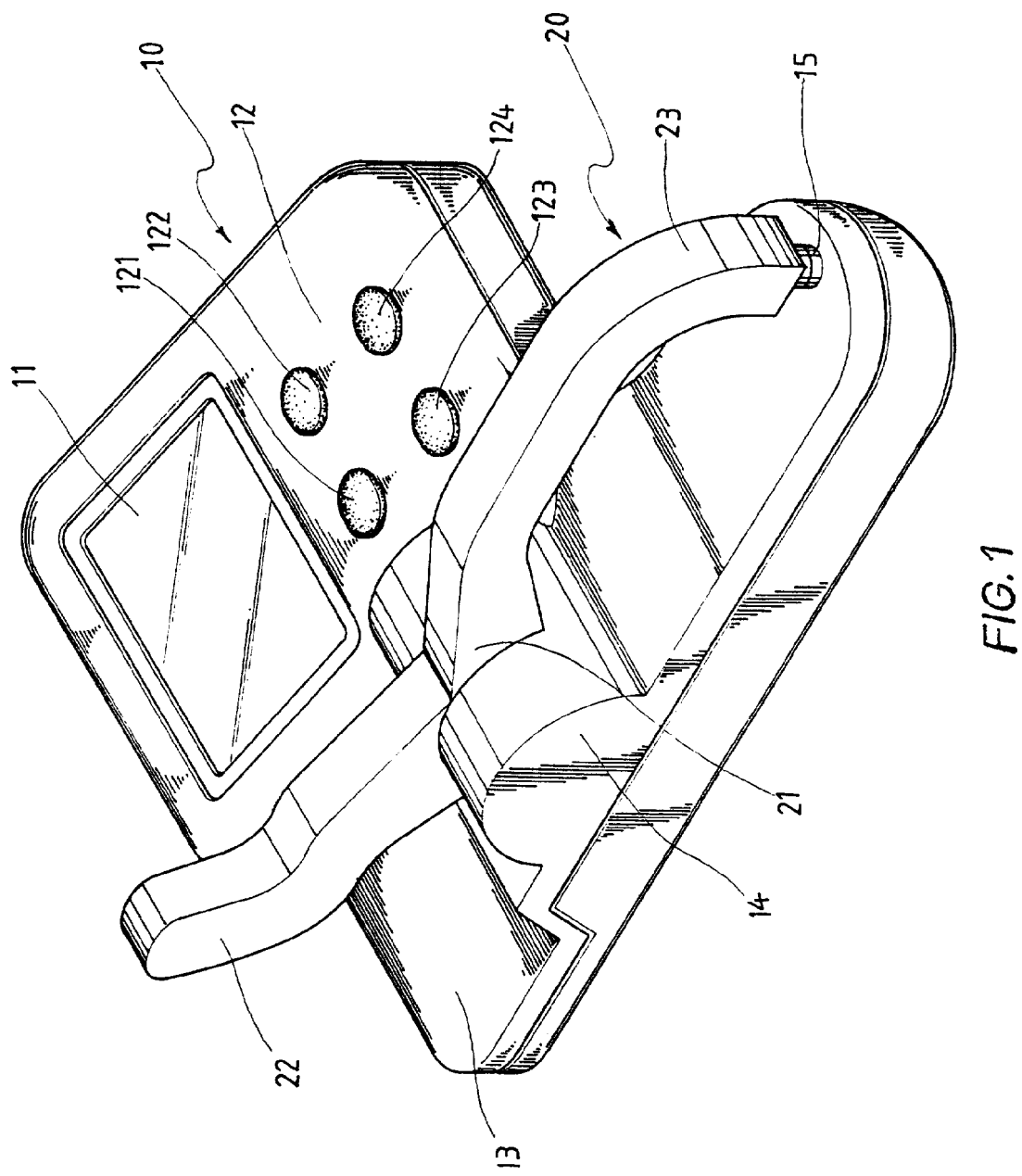
FIG. 1 is a perspective of an electronic fat gauge according to a preferred embodiment of the present invention.
Figure 2:
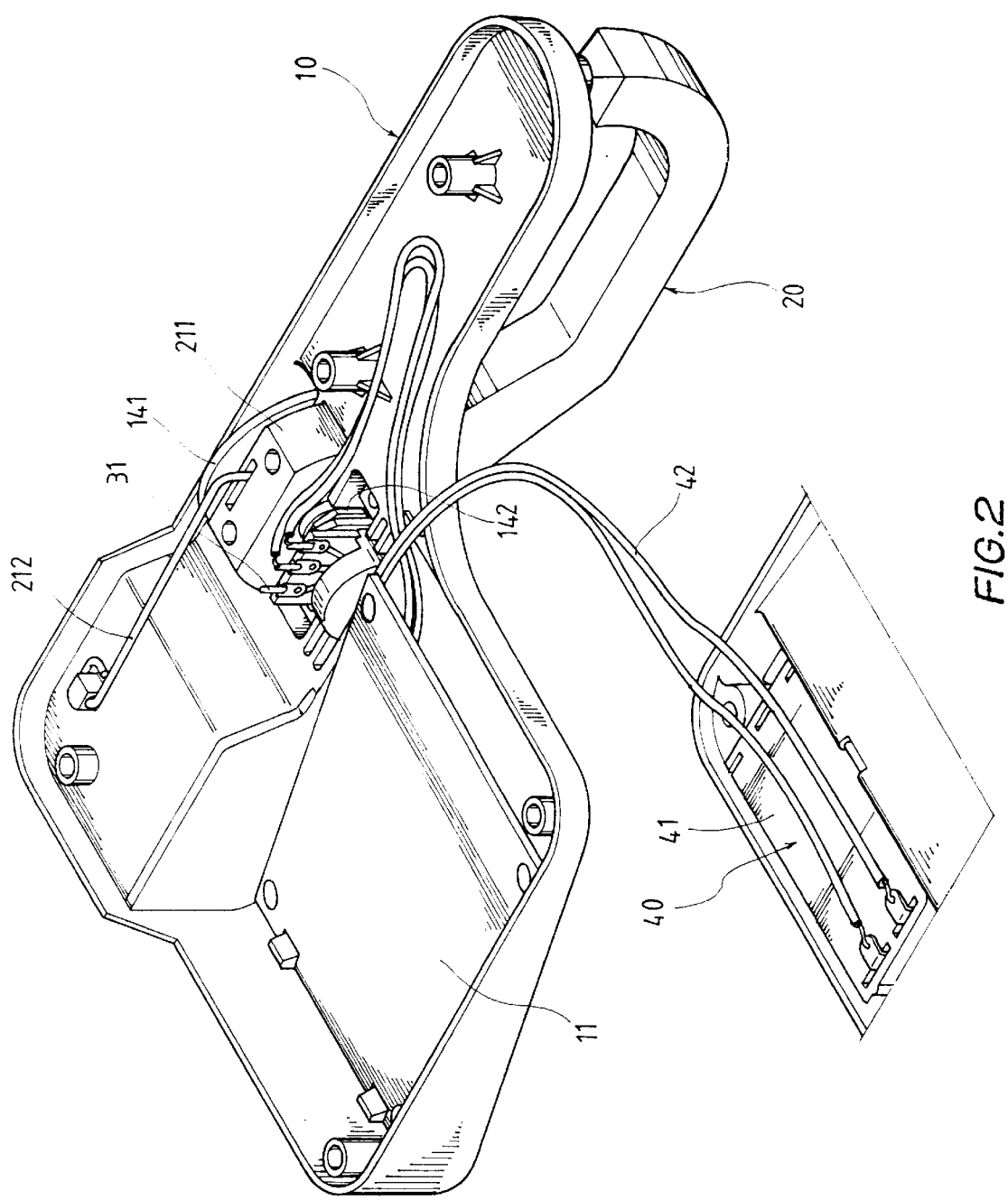
FIG. 2 is a perspective bottom view of the electronic fat gauge of FIG. 1 with a bottom plate thereof removed to show internal structure thereof.
Figure 3:
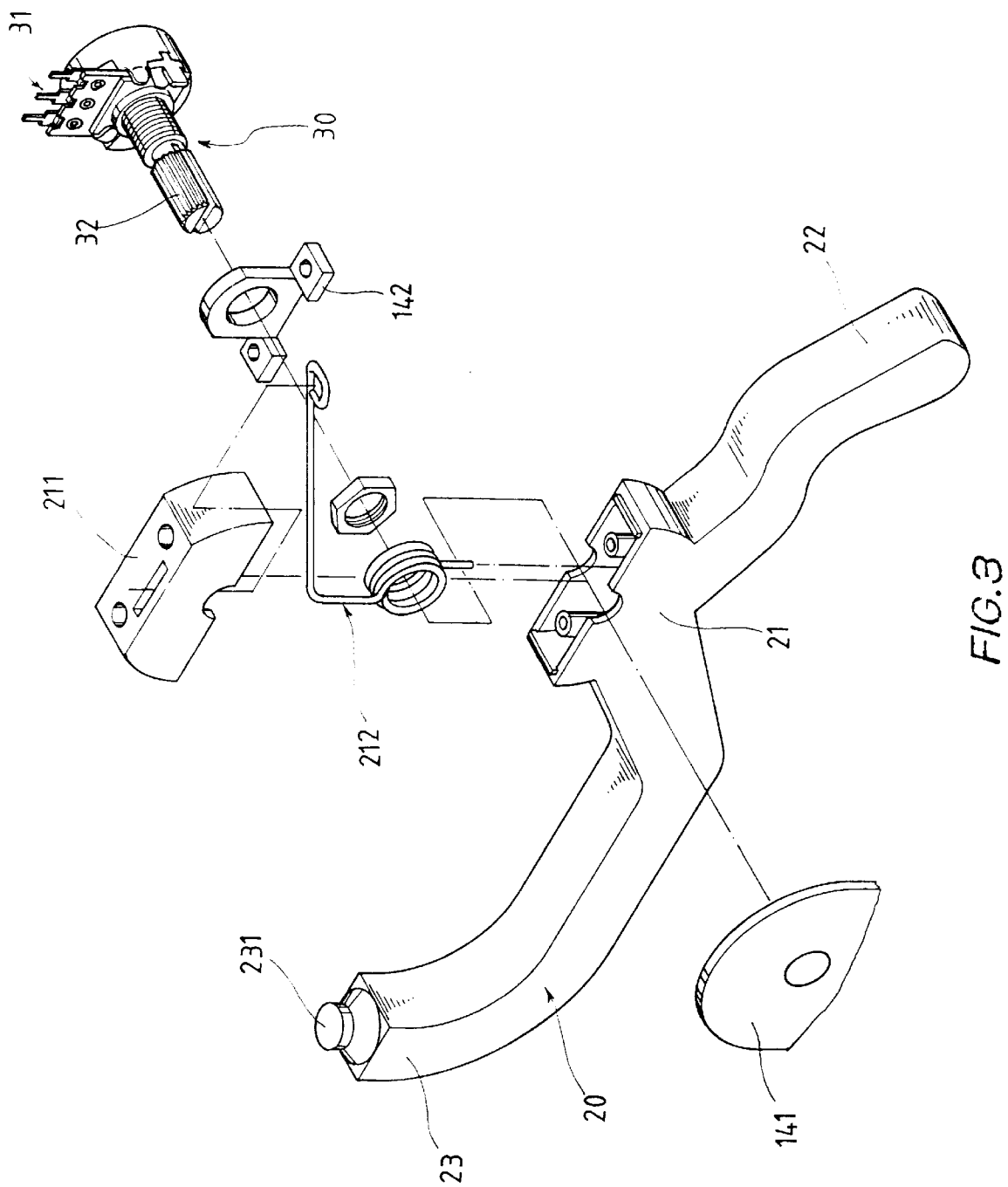
FIG. 3 is an exploded perspective of a clamping lever of the electronic fat gauge of FIG. 1.

Please refer to FIGS. 1, 2 and 3 in which an electronic fat gauge according to a preferred embodiment of the present invention is shown. The electronic fat gauge mainly includes a main body 10 and a clamping lever 20 pivotally connected to the main body 10.

The main body 10 defines an inner space with a predetermined height and preferably has a substantially P-shaped configuration to allow easy operation of it by a user with only one hand. The right side of the substantially P-shaped main body 10, as viewing in front of the fat gauge, is a transversely extended control portion on which a liquid crystal display 11 and a console 12 are provided. On the console 12, push buttons for different purposes are provided. Push buttons shown in FIG. 1 include an ON/OFF button 121, an AGE button 122, a SEX button 123, and a HOLD button 124. By depressing the ON/OFF button 121, the electronic fat gauge is switched on or off. By depressing the AGE and SEX buttons, age and sex of the user are shown on the liquid crystal display 11 for use as a basis to calculate a measured result. By depressing the HOLD button 124, a calculated value could be shown in the liquid crystal display 11 for a prolonged time for the user to check. And, the left side of the P-shaped main body 10, as viewing in front of the fat gauge, is a longitudinally extended and elongated seat portion. A top part of the seat portion to the left of the liquid crystal display 11 has a reduced height to form a lowered front zone 13. A middle part of the seat portion to the left of the console 12 is provided with a transverse pivot seat 14. A bottom part of the seat portion vertically projected from the transversely extended control portion is provided near a free end with a flat-topped projection 15.

The clamping lever 20 includes a middle pivot portion 21 rotatably mounted in the pivot seat 14, so that the clamping lever 20 is allowed to move in lever motion with the middle pivot portion 21 as a fulcrum. A shorter depressing arm 22 extends from the middle pivot portion 21 to locate above the lowered front zone 13 in an upward inclined position, such that a large angle is contained between the depressing arm 22 and the lowered front zone 13 when the depressing arm 22 is not depressed. A longer curved measuring arm 23 extends from the middle pivot portion 21 opposite to the shorter depressing arm 22, such that the longer measuring arm 23 could be pivotally lifted and widely opened relative to the rear part of the seat portion of the main body 10 when the depressing arm 22 is depressed toward the lowered front zone 13. A free end of the longer curved measuring arm 23 extends downward to form a dimension-reduced projection 231 corresponding to the flat-topped projection 15 on the main body 10. When the depressing arm 22 is not depressed, the longer measuring arm 23 is located above the rear part of the seat portion of the main body 10 with the dimension-reduced projection 231 pressing against the flat-topped projection 15. The flat-topped projection 15 therefore serves as a basic point or zero point in measuring fat.

Figure 4:
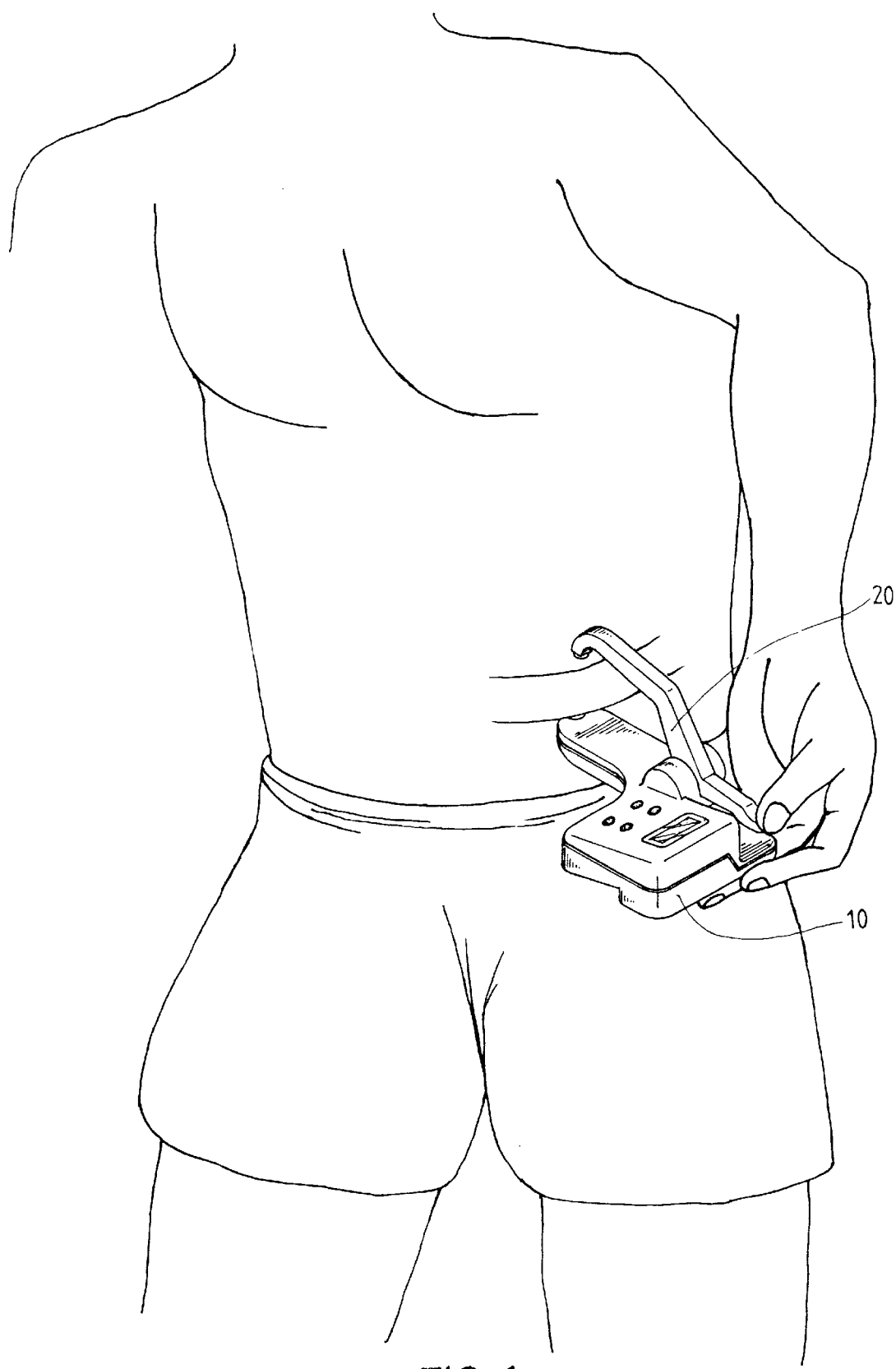
FIG. 4 exemplifies the use of the electronic fat gauge of the present invention to measure fat at the user's belly.

Since the curved measuring arm 23 of the clamping lever 20 is long and permits large open angle, the fat gauge of the present invention could be conveniently handled to clamp any fatty area on the user's body for measuring purpose, as shown in FIG. 4.

As can be clearly seen from FIGS. 2 and 3, an electronic control circuit 40 including a circuit board 41 and conductors 42 is provided inside the main body 10. The conductors 42 electrically connect the control circuit 40 to the liquid crystal display 11 and outputs 31 of a variable resistor 30. The variable resistor 30 is mounted in an inner space of the pivot seat 14 with an adjusting and controlling shaft 32 of the variable resistor 30 extended through two fixed shaft holding plates 141 and 142 to locate between them. A covering member 211 having a configuration corresponding to that of a lower part of the middle pivot portion 21 of the clamping lever 20 is screwed to a bottom of the middle pivot portion 21, so that the adjusting and controlling shaft 32 of the variable resistor 30 transversely located between the two fixed shaft holding plates 141, 142 is further vertically locked between the middle pivot portion 21 and the covering member 211. Whereby, when the depressing arm 22 of the clamping lever 20 is depressed and causes the middle pivot portion 21 to rotate, the adjusting and controlling shaft 32 locked to the middle pivot portion 21 is brought to rotate synchronously. That is, the depressed angle of the depressing arm 22 equals to an open angle of the measuring arm 23, and when the adjusting and controlling shaft 32 turns along with the middle pivot portion 21, it converts the open angle of the curved measuring arm 23 into an electronic signal that is then sent to the electronic control circuit 40, where the signal is further converted into a value showing the measuring result for display in the liquid crystal display 11.

Figure 5:
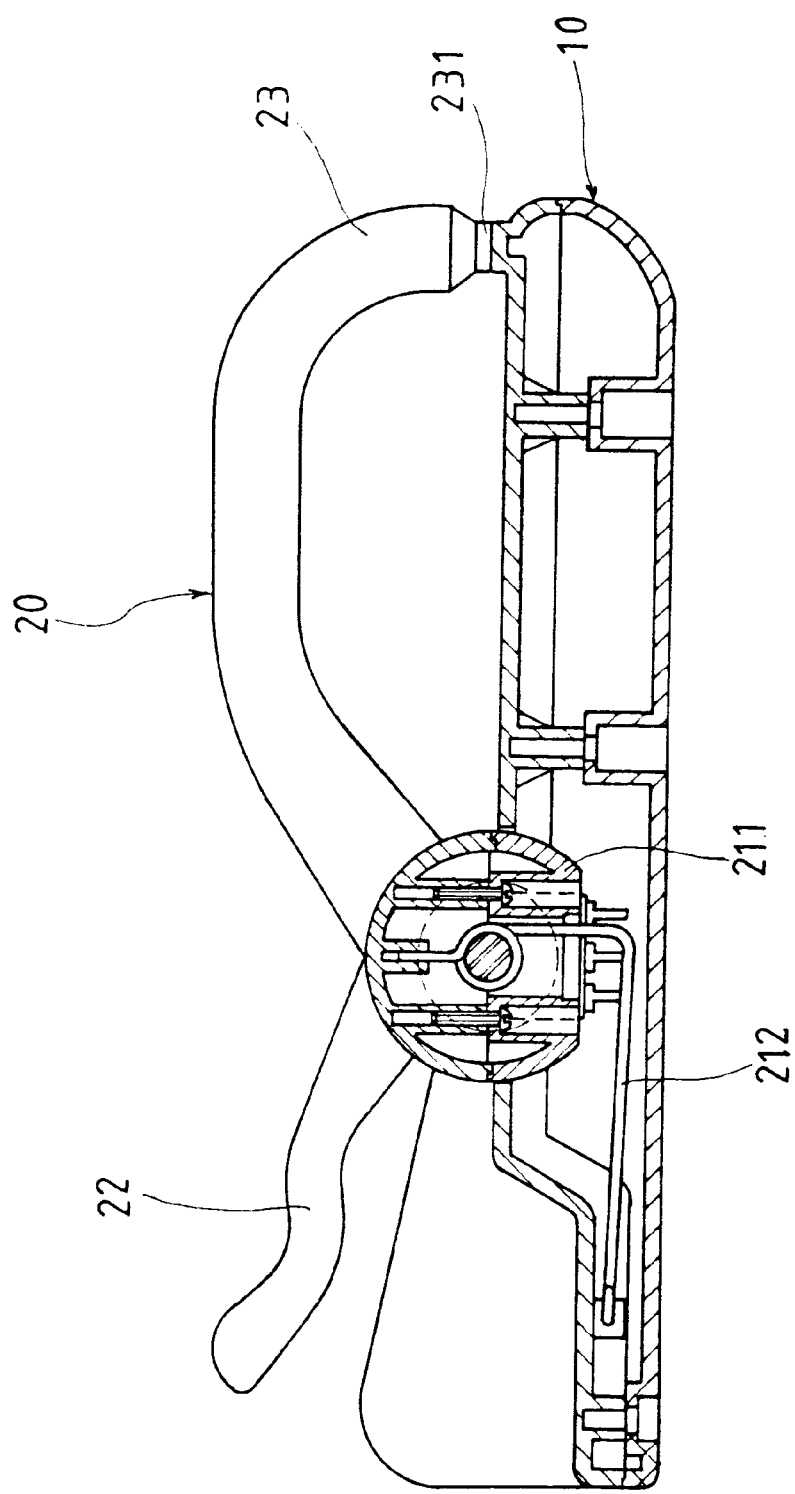
FIG. 5 is a sectional view of the electronic fat gauge of FIG. 1 with the measuring arm of the clamping lever in a closed position.
Figure 6:
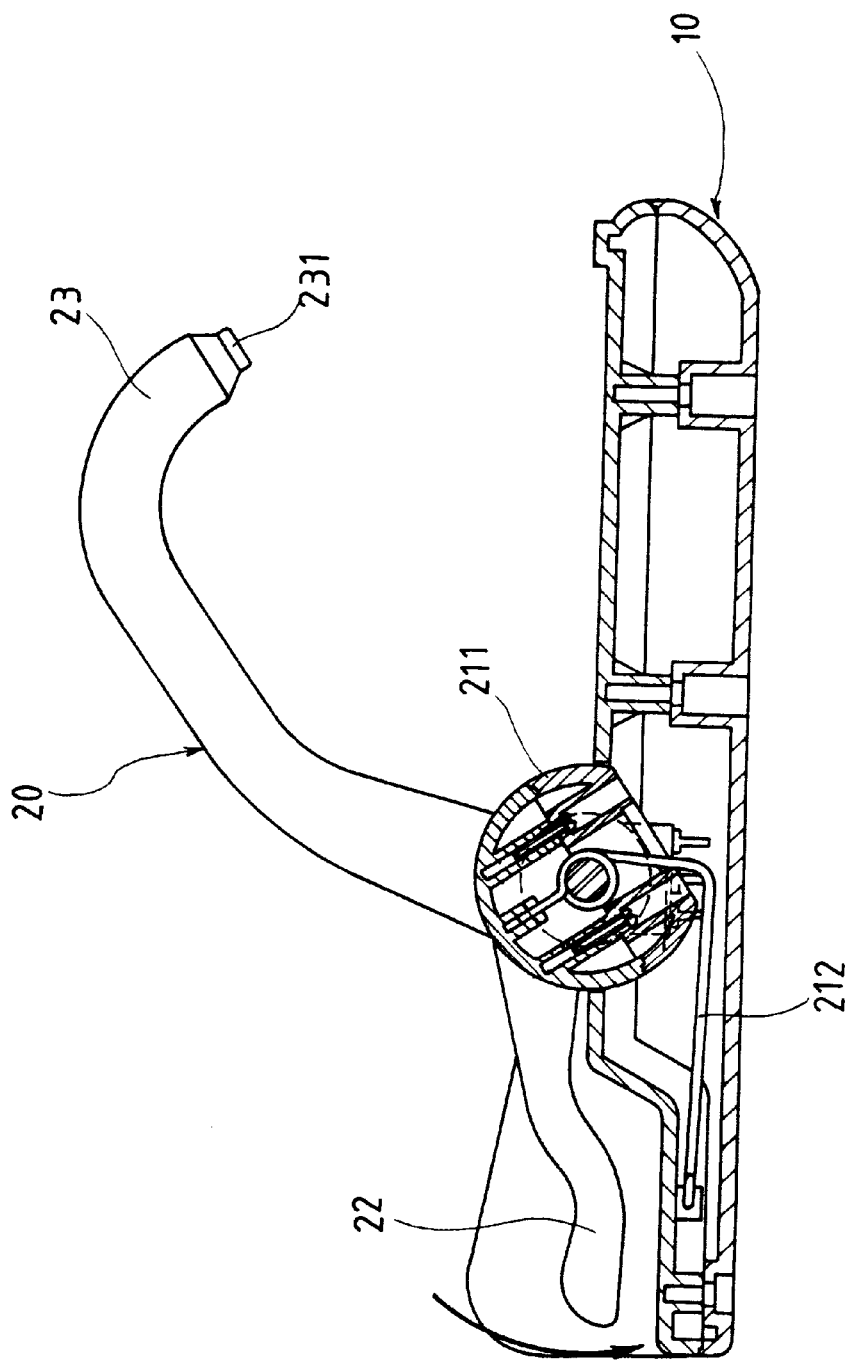
FIG. 6 is a sectional view of the electronic fat gauge of FIG. 1 with the measuring arm of the clamping lever in an opened position.

A return spring 212 is disposed between the middle pivot portion 21 and the covering member 211 with an end of the return spring 212 fixedly connected to the middle pivot portion 21 and another end of the return spring 212 extended down into the main body 10 and fixedly connected to a predetermined point. An elastic restoring force of the return spring 212 allows the opened measuring arm 23 of the clamping lever 20 to elastically return to the zero point (that is, the flat-topped projection 15), as shown in FIGS. 5 and 6. The provision of the return spring 212 facilitates firm clamping of fatty area with the measuring arm 23 and convenient operation of the fat gauge by the user.

What is claimed is:

1. An electronic fat gauge comprising a main body and a clamping lever pivotally connected to said main body to move in lever motion;

said main body defines an inner space with a predetermined height and has a substantially P-shaped configuration; a right side of said substantially P-shaped main body, as viewed in front of said fat gauge, being a transversely extended control portion on which a liquid crystal display and a console are provided, said console having push buttons provided thereon for different purposes; a left side of said substantially P-shaped main body being a longitudinally extended and elongated seat portion that further including a lowered top zone, a middle pivot seat, and a bottom extended part having a flat-topped projection provided near a free end thereof;

said clamping lever including a middle pivot portion rotatably mounted in said pivot seat to allow said clamping lever to move in lever motion relative to said main body, a shorter depressing arm extended from one end of said middle pivot portion to upward extend above said lowered top zone and define an angle between said depressing arm and said lowered top zone, and a longer measuring arm extended from another end of said middle pivot portion opposite to said shorter depressing arm to extend above said bottom extended part of said seat portion of said main body;

a variable resistor mounted in an inner space of said pivot seat with an adjusting and controlling shaft of said variable resistor horizontally extended through two fixed shaft holding plates said adjusting and controlling shaft being locked between said middle pivot portion of said clamping lever and a covering member screwed to a bottom of said middle pivot portion, such that said adjusting and controlling shaft always rotates along with said middle pivot portion of said clamping lever; and an electronic control circuit provided inside said main body and electrically connect to said liquid crystal display and said variable resistor;

whereby when said depressing arm of said clamping lever is depressed and causes said middle pivot portion to rotate, said adjusting and controlling shaft of said variable resistor is brought to rotate synchronously with said measuring arm, wherein the position of said measuring arm is converted into an electronic signal that is then sent to said electronic control circuit, where said signal is further converted into a value measurement for displaying in said liquid crystal display.

2. An electronic fat gauge as claimed in claim 1, further comprises a return spring disposed between said middle pivot portion and said adjusting and controlling shaft of said variable resistor to allow said measuring arm of said clamping lever to elastically return from an opened position to a closed position on said main body.

3. An electronic fat gauge as claimed in claim 1, wherein said depressing arm and said lowered top zone together contain a large angle between them, so that a full depression of said depressing arm toward said lowered top zone causes said measuring arm to widely open by an equal large angle that facilitates easy clamping of a fatty area of a user's body between said clamping lever and said bottom extended part of said main body, and said measuring arm being provided at a free end with a dimension-reduced projection that is seated on said flat-topped projection when said measuring arm is in a closed position on said main body.

* * * * *